(12) United States Patent
Harada

(10) Patent No.: US 9,442,283 B2
(45) Date of Patent: Sep. 13, 2016

(54) ENDOSCOPIC OBJECTIVE LENS AND ENDOSCOPE

(71) Applicant: FUJIFILM CORPORATION, Tokyo (JP)

(72) Inventor: Keisuke Harada, Saitama-ken (JP)

(73) Assignee: FUJIFILM Corporation, Tokyo (JP)

(*) Notice: Subject to any disclaimer, the term of this patent is extended or adjusted under 35 U.S.C. 154(b) by 39 days.

(21) Appl. No.: 14/601,428

(22) Filed: Jan. 21, 2015

(65) Prior Publication Data

US 2015/0131171 A1    May 14, 2015

Related U.S. Application Data

(63) Continuation of application No. PCT/JP2013/004087, filed on Jul. 2, 2013.

(30) Foreign Application Priority Data

Jul. 23, 2012   (JP) ................................ 2012-162666

(51) Int. Cl.
| | | |
|---|---|---|
| G02B 21/02 | (2006.01) | |
| G02B 3/02 | (2006.01) | |
| G02B 9/04 | (2006.01) | |
| A61B 1/00 | (2006.01) | |
| G02B 23/24 | (2006.01) | |
| G02B 23/26 | (2006.01) | |
| G02B 13/00 | (2006.01) | |

(52) U.S. Cl.
CPC ........... *G02B 23/243* (2013.01); *G02B 13/006* (2013.01); *G02B 23/26* (2013.01); *A61B 1/00096* (2013.01)

(58) Field of Classification Search
CPC .. G02B 23/243; G02B 13/006; G02B 23/26; A61B 1/00096
USPC ........... 359/661, 717, 738, 739, 793; 348/65
See application file for complete search history.

(56) References Cited

U.S. PATENT DOCUMENTS

| | | |
|---|---|---|
| 5,270,825 A | 12/1993 | Takasugi et al. |
| 5,828,498 A | 10/1998 | Sekiya et al. |
| 7,158,314 B2 | 1/2007 | Fujii |
| 2005/0200971 A1 | 9/2005 | Fujii |

FOREIGN PATENT DOCUMENTS

| | | |
|---|---|---|
| JP | 3-126006 | 5/1991 |
| JP | 8-122634 | 5/1996 |
| JP | 2000-19393 | 1/2000 |
| JP | 2005-257912 | 9/2005 |
| JP | 4373819 | 9/2009 |

OTHER PUBLICATIONS

International Search Report—PCT/JP2013/004087—Oct. 22, 2013.

*Primary Examiner* — William Choi
(74) *Attorney, Agent, or Firm* — Young & Thompson

(57) ABSTRACT

An endoscopic objective lens consists of a negative first lens group, a stop, and a positive second lens group, disposed in order from the object side. The first lens group is composed of a cemented lens formed of a first lens and a second lens with a concave surface on the image side cemented in order from the object side. The second lens group is composed of a positive single third lens and a cemented lens formed of a fourth lens and a fifth lens, either of which being a positive lens and the other being a negative lens, and having a positive refractive power, disposed in order from the object side. The endoscopic objective lens satisfies given conditional expressions related to Abbe numbers of the first and second lenses and radii of curvature of the image side and object side surfaces of the second lens.

17 Claims, 11 Drawing Sheets

EXAMPLE 1

FIG.1  EXAMPLE 1
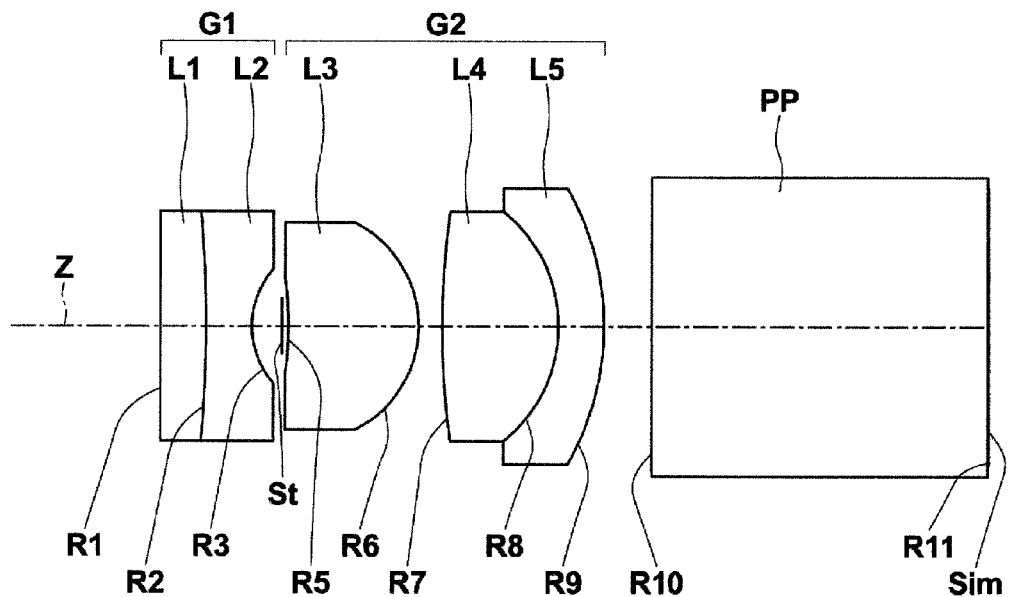
FIG.2  EXAMPLE 2
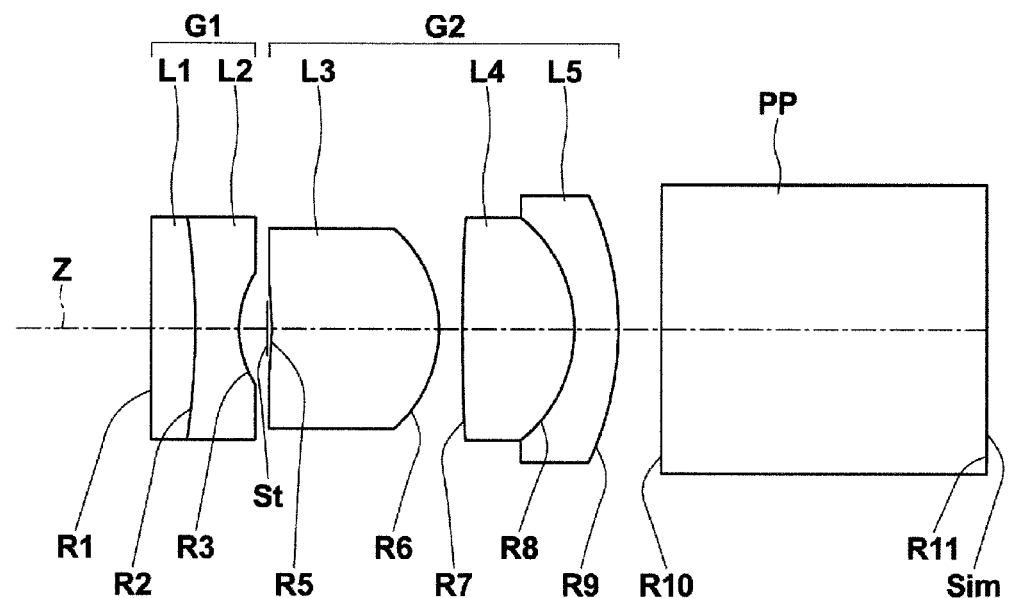

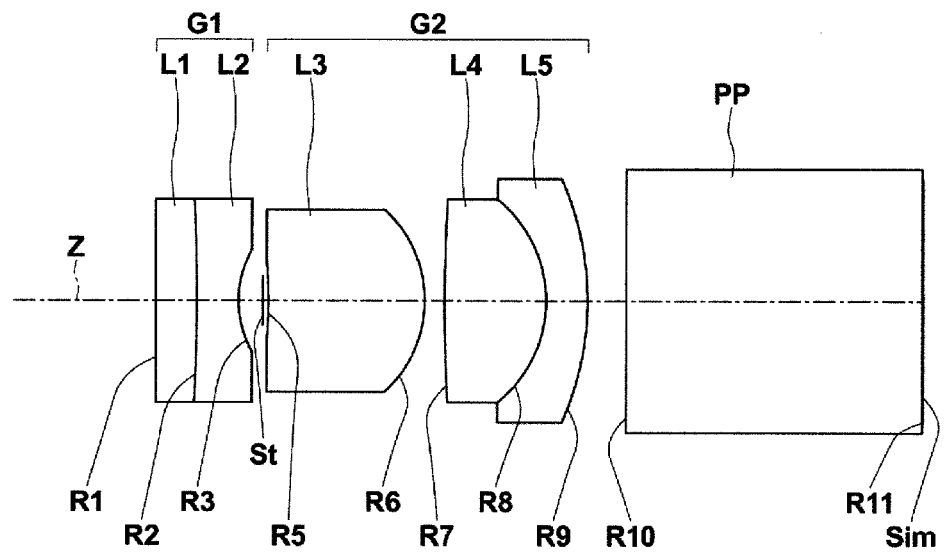
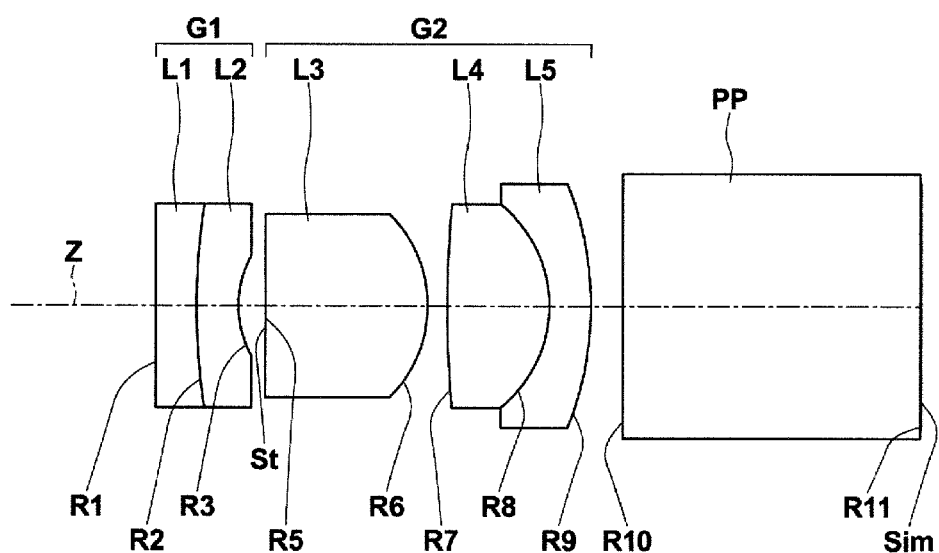

FIG.5  EXAMPLE 5
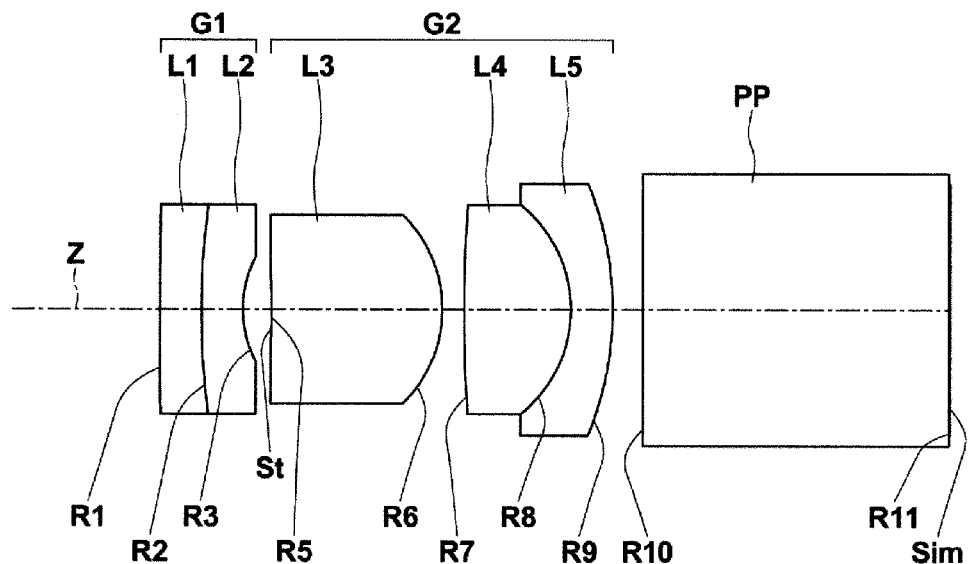
FIG.6  EXAMPLE 6
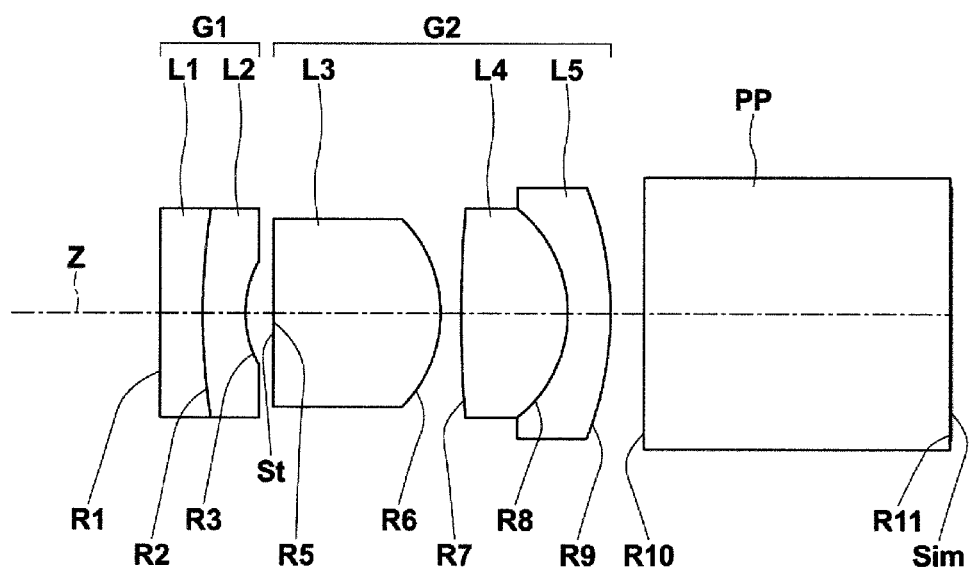

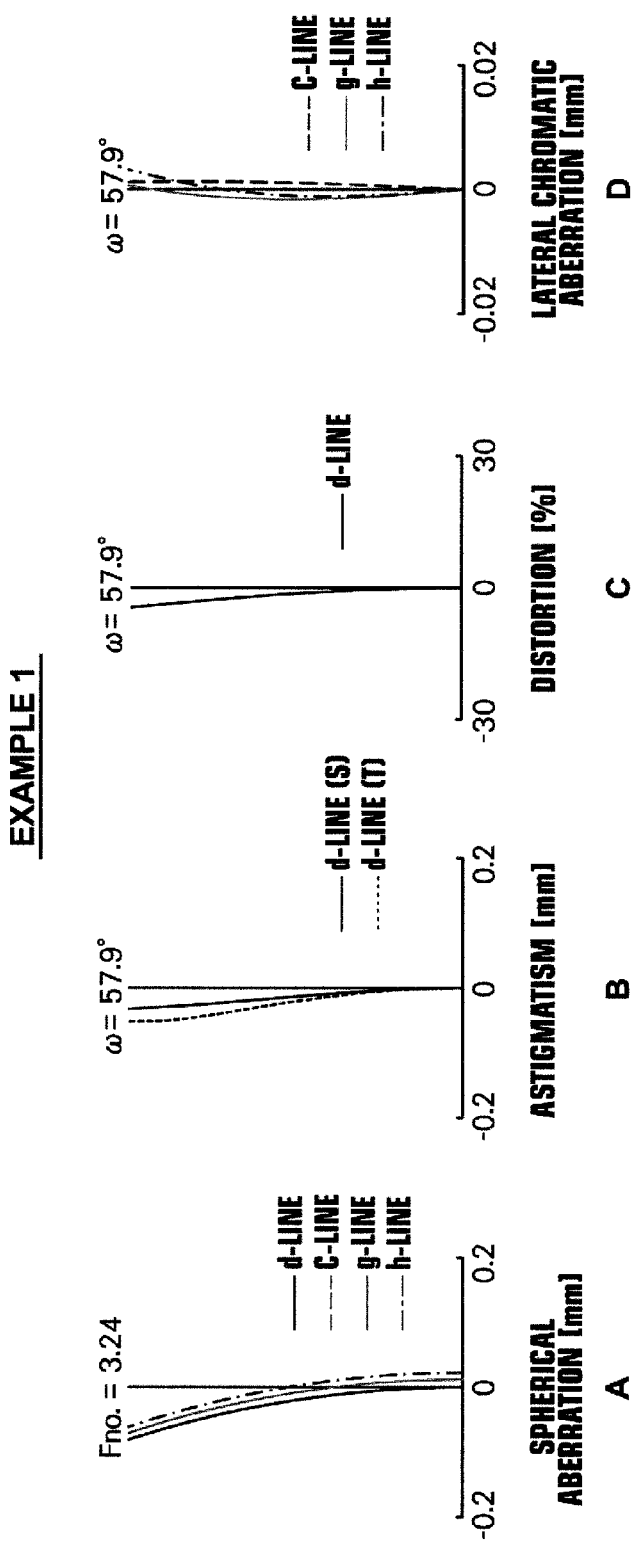

FIG.9 EXAMPLE 3

ENDOSCOPIC OBJECTIVE LENS AND ENDOSCOPE

CROSS-REFERENCE TO RELATED APPLICATIONS

This application is a Continuation of PCT International Application No. PCT/JP2013/004087 filed on Jul. 2, 2013, which claims priority under 35 U.S.C. §119 (a) to Japanese Patent Application No. 2012-162666 filed on Jul. 23, 2012. Each of the above applications is hereby expressly incorporated by reference, in its entirety, into the present application.

BACKGROUND OF THE INVENTION

1. Technical Field

The present invention relates to an endoscopic objective lens and an endoscope.

2. Background Art

Heretofore, endoscopes have been used in the field of medicine to observe, for example, stomachs and esophagi. A peroral endoscope which is to be inserted from a mouth may sometimes give distress of nausea or discomfort to a patient due to touching of the endoscope to the root of the tongue or on the inner throat when the endoscope is inserted into the patient. In recent years, downsized and diameter-reduced endoscopes, including a nasal endoscope downsized enough to be inserted from a nose, have been used in order to alleviate such distress. When considering downsizing and diameter reduction of an endoscope, it is necessary to downsize a distal end portion of the insertion section. The distal end portion includes an observation objective lens, an illumination section, a treatment tool insertion opening, an air and water supply nozzle for cleaning the surface of the objective lens, and the like.

Among them, improvements have been made with respect to the objective lens, including reductions in the number of lenses, in overall length and in lens diameter for the downsizing. For example, an objective lens having a lens configuration constituted by only one negative lens on the object side of the stop is proposed for the downsizing of the distal end portion. Further, an objective lens having a lens configuration in which the object side of the stop is constituted by only one cemented lens is proposed in Japanese Unexamined Patent Publication No. 8 (1996)-122634 and Japanese Patent No. 4373819.

DISCLOSURE OF THE INVENTION

The configuration in which only one negative lens is disposed on the object side of the stop, as described above, may often result in insufficient correction of longitudinal chromatic aberration and lateral chromatic aberration, in addition to astigmatism and field curvature. In endoscopic observation, it is practiced that a fine blood vessel pattern and a shade of a lesion are observed. If color bleeding occurs due to insufficient correction of chromatic aberration or some other reasons, it becomes problematic to implement prompt and appropriate treatment. Therefore, a due consideration should be given to correct chromatic correction sufficiently along with the downsizing. To that end, it may be conceivable, for example, to dispose a cemented lens on each of the object side and the image side of the stop.

Japanese Unexamined Patent Publication No. 8 (1996)-122634 and Japanese Patent No. 4373819 describe configurations in which only one cemented lens is disposed on the object side of the stop and one cemented lens is disposed on each of the object side and the image side of the stop. In these configurations, as the materials of the cemented lenses, in particular, as the materials of the negative lenses of the cemented lenses, those having relatively high Abbe numbers are selected. But, they still do not get into the region of low dispersion materials which are supposed to have highest Abbe number and it can be thought that they has not yet attained optimum chromatic aberration correction. Further, in the configuration described in Japanese Unexamined Patent Publication No. 8 (1996)-122634 and Japanese Patent No. 4373819 in which only one cemented lens is disposed on the object side of the stop, the distance between the cemented lens and the stop is large, which increases the ray height at the most object side lens and the outer diameter of the lens is increased, thereby causing a problem of impeding the diameter reduction.

The present invention has been developed in view of the circumstances described above, and it is an object of the present invention to provide an endoscopic objective lens that allows downsizing, diameter reduction, and sufficient correction of chromatic aberration to obtain a favorable image, and an endoscope equipped with the endoscopic object lens.

A first endoscopic objective lens of the present invention consists essentially of a first lens group having a negative refractive power, a stop, and a second lens group having a positive refractive power, disposed in order from the object side, in which the first lens group is composed of a cemented lens formed of a first lens and a second lens with a concave surface on the image side cemented in order from the object side, the second lens group is composed of a positive single third lens and a cemented lens formed of a fourth lens and a fifth lens, either of which being a positive lens and the other being a negative lens, and having a positive refractive power as a whole, disposed in order from the object side, and the endoscopic object lens satisfies conditional expressions (1) and (2) given below:

$$25 < vd2 - vd1 < 60 \tag{1}$$

$$-1.6 < (R3+R2)/(R3-R2) < -0.5 \tag{2}$$

where vd1: Abbe number of the first lens with respect to the d-line, vd2: Abbe number of the second lens with respect to the d-line, R2: radius of curvature of the object side surface of the second lens, and R3: radius of curvature of the image side surface of the second lens.

The first endoscopic objective lens of the present invention more preferably satisfies at least one of conditional expressions (1') and (2') given below:

$$27 < vd2 - vd1 < 58 \tag{1'}$$

$$-1.5 < (R3+R2)/(R3-R2) < -0.6 \tag{2'}$$

A second endoscopic objective lens of the present invention consists essentially of a first lens group having a negative refractive power, a stop, and a second lens group having a positive refractive power, disposed in order from the object side, in which the first lens group is composed of a cemented lens formed of a first lens and a second lens with a concave surface on the image side cemented in order from the object side, the second lens group is composed of a positive single third lens and a cemented lens formed of a fourth lens and a fifth lens, either of which being a positive lens and the other being a negative lens, and having a positive refractive power as a whole, disposed in order from the object side, and the endoscopic object lens satisfies conditional expressions (3) and (4) given below:

$$1<|R2/R3|<30 \qquad (3)$$

$$0.40<|DS \times fG1/(f \times (DS-fG1))|<0.60 \qquad (4)$$

where

R2: radius of curvature of the object side surface of the second lens,

R3: radius of curvature of the image side surface of the second lens,

DS: distance on the optical axis from the object side surface of the first lens to the stop, fG1: focal length of the first lens group, and f: focal length of the entire system.

The second endoscopic objective lens of the present invention more preferably satisfies at least one of conditional expressions (3') and (4') given below:

$$3|R2/R3|<25 \qquad (3')$$

$$0.4593|DS \times fG1/(f \times (DS-fG1))|<0.55 \qquad (4').$$

The first and the second endoscopic objective lenses of the present invention preferably satisfy a conditional expression (5) given below, and more preferably satisfies a conditional expression (5') given below:

$$|D1/R2|1<0.10 \qquad (5)$$

$$0.01<|D1/R2|1<0.08 \qquad (5')$$

where

D1: center thickness of the first lens.

The first and the second endoscopic objective lenses of the present invention preferably satisfy a conditional expression (6) given below, and more preferably satisfies a conditional expression (6') given below:

$$0.80<Bf/f<1.38 \qquad (6)$$

$$1.00<Bf/f<1.37 \qquad (6')$$

where

Bf: back focus of the entire system, and f: focal length of the entire system.

The first and the second endoscopic objective lenses of the present invention preferably satisfy a conditional expression (7) given below, and more preferably satisfies a conditional expression (7') given below:

$$20<vdp-vdn<40 \qquad (7)$$

$$22<vdp-vdn<38 \qquad (7')$$

where vdp: Abbe number of the positive lens of the cemented lens in the second lens group with respect to the d-line, and vdn: Abbe number of the negative lens of the cemented lens in the second lens group with respect to the d-line.

The first and the second endoscopic objective lenses of the present invention preferably satisfy conditional expressions (8) and (9) given below, and more preferably satisfies at least one of conditional expressions (8') and (9') given below:

$$1.85<Nd1<1.92 \qquad (8)$$

$$35<vd1<45 \qquad (9)$$

$$1.86<Nd1<1.90 \qquad (8')$$

$$38<vd1<43 \qquad (9')$$

where

Nd1: refractive index of the first lens with respect to the d-line, and vd1: Abbe number of the first lens with respect to the d-line.

The foregoing "essentially" in the context of "consists essentially of ----------" intends that the endoscopic objective lens may include a lens having substantially no refractive power, an optical element other than a lens, such as a stop, a cover glass, and the like, a lens flange, a lens barrel, and an image sensor, in addition to the constituent elements. Further, the term "first lens group is composed of ----------" and the term "second lens group is composed of ----------" as used herein also refers to in a substantive sense.

The surface shapes and the signs of refractive powers of the aforementioned lenses are considered in the paraxial region if they include aspherical surfaces.

The sign of a radius of curvature is positive for a surface shape with a convex surface on the object side and negative for a surface shape with a convex surface on the image side.

The term "single lens" as used herein refers to one lens not cemented.

An endoscope of the present invention is equipped with the endoscopic objective lens of the present invention described above.

The endoscopic objective lens of the present invention is a retrofocus type lens system composed of five lenses, in which a cemented lens is disposed on each of the object side and the image side of the stop, and each lens is optimally formed to satisfy given conditional expressions. This allows downsizing with reduced diameter to be achieved and a favorable image with longitudinal chromatic aberration and lateral chromatic aberration being corrected sufficiently to be obtained.

The endoscope of the present invention is equipped with the endoscopic objective lens of the present invention, so that the downsizing with reduced diameter of the insertion section may be achieved and a favorable image with good color reproducibility may be obtained.

BRIEF DESCRIPTION OF DRAWINGS

FIG. 1 is a cross-sectional view of an endoscopic objective lens of Example 1 of the present invention, illustrating the configuration thereof.

FIG. 2 is a cross-sectional view of an endoscopic objective lens of Example 2 of the present invention, illustrating the configuration thereof.

FIG. 3 is a cross-sectional view of an endoscopic objective lens of Example 3 of the present invention, illustrating the configuration thereof.

FIG. 4 is a cross-sectional view of an endoscopic objective lens of Example 4 of the present invention, illustrating the configuration thereof.

FIG. 5 is a cross-sectional view of an endoscopic objective lens of Example 5 of the present invention, illustrating the configuration thereof.

FIG. 6 is a cross-sectional view of an endoscopic objective lens of Example 6 of the present invention, illustrating the configuration thereof.

A to D of FIG. 7 show aberration diagrams of the endoscopic objective lens of Example 1 of the present invention.

Figure 8:
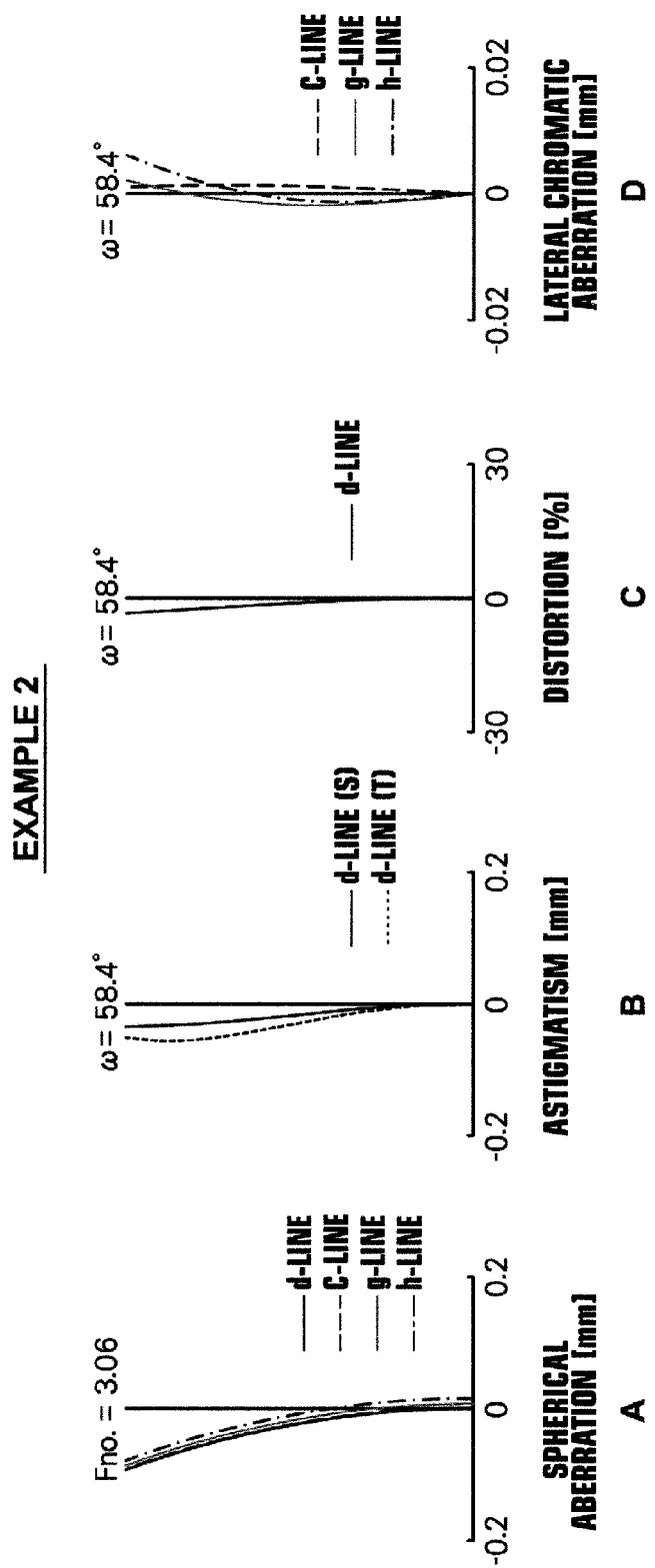

A to D of FIG. 8 show aberration diagrams of the endoscopic objective lens of Example 2 of the present invention.

Figure 9:
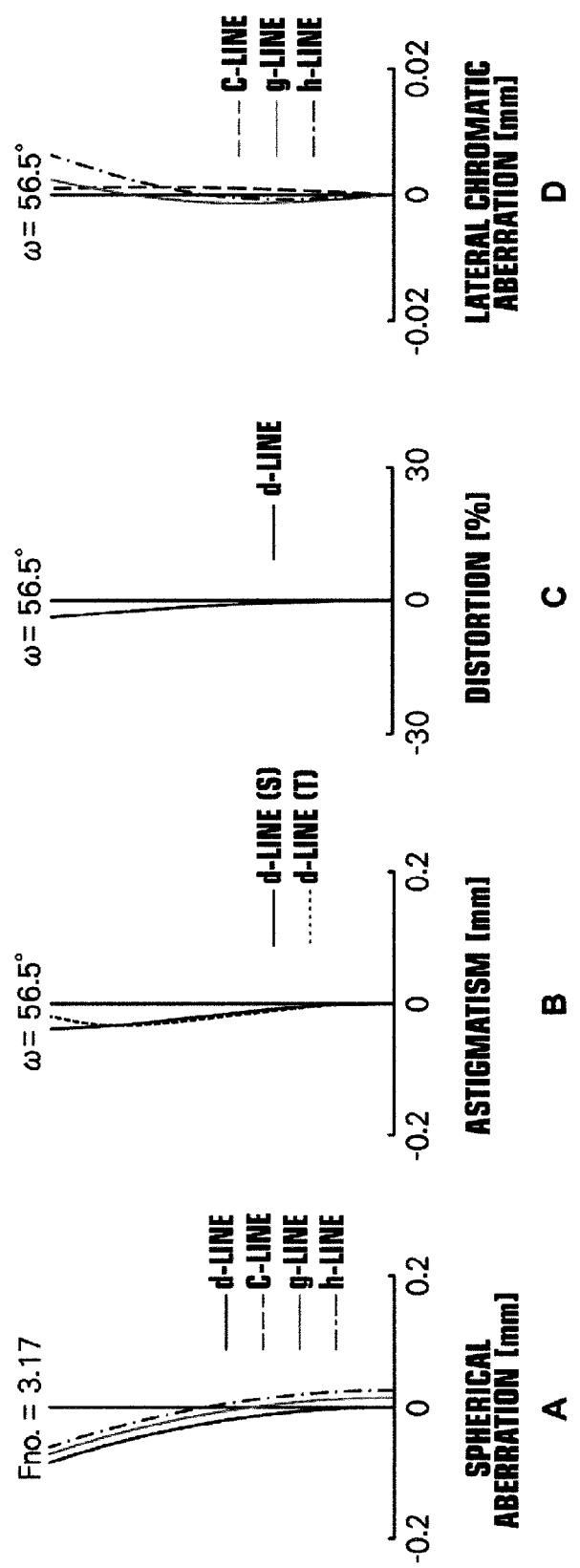

A to D of FIG. 9 show aberration diagrams of the endoscopic objective lens of Example 3 of the present invention.

Figure 10:
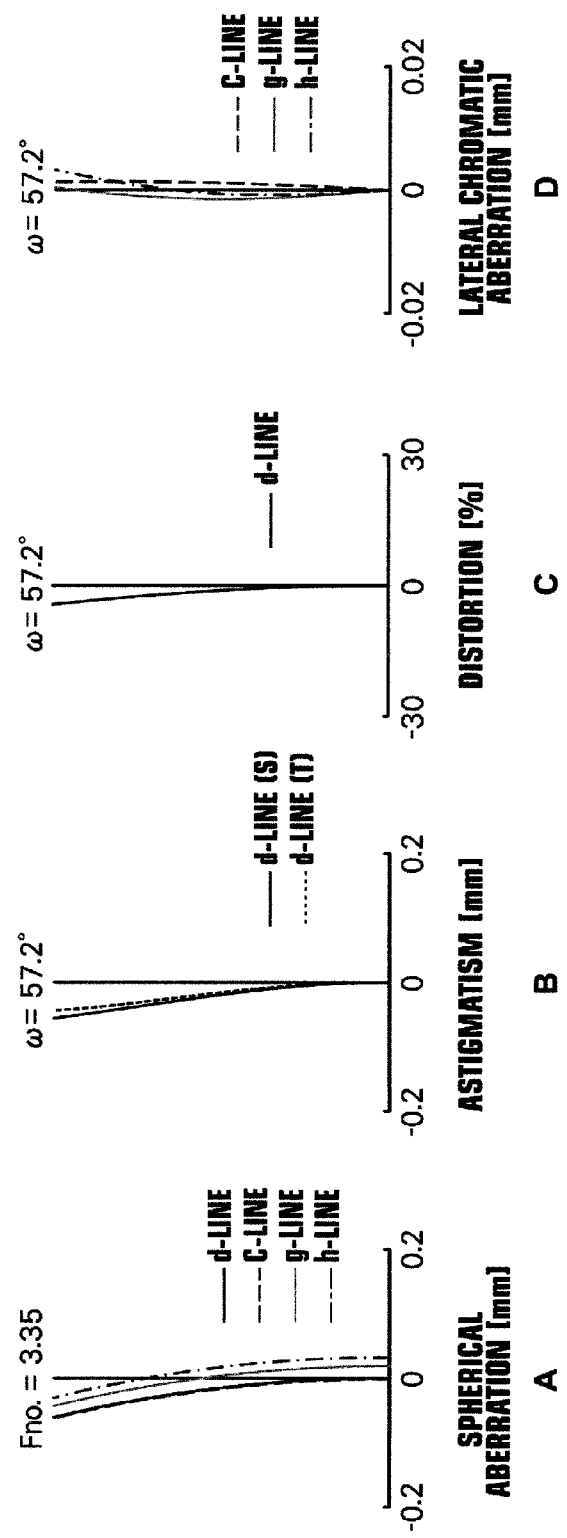

A to D of FIG. 10 show aberration diagrams of the endoscopic objective lens of Example 4 of the present invention.

Figure 11:
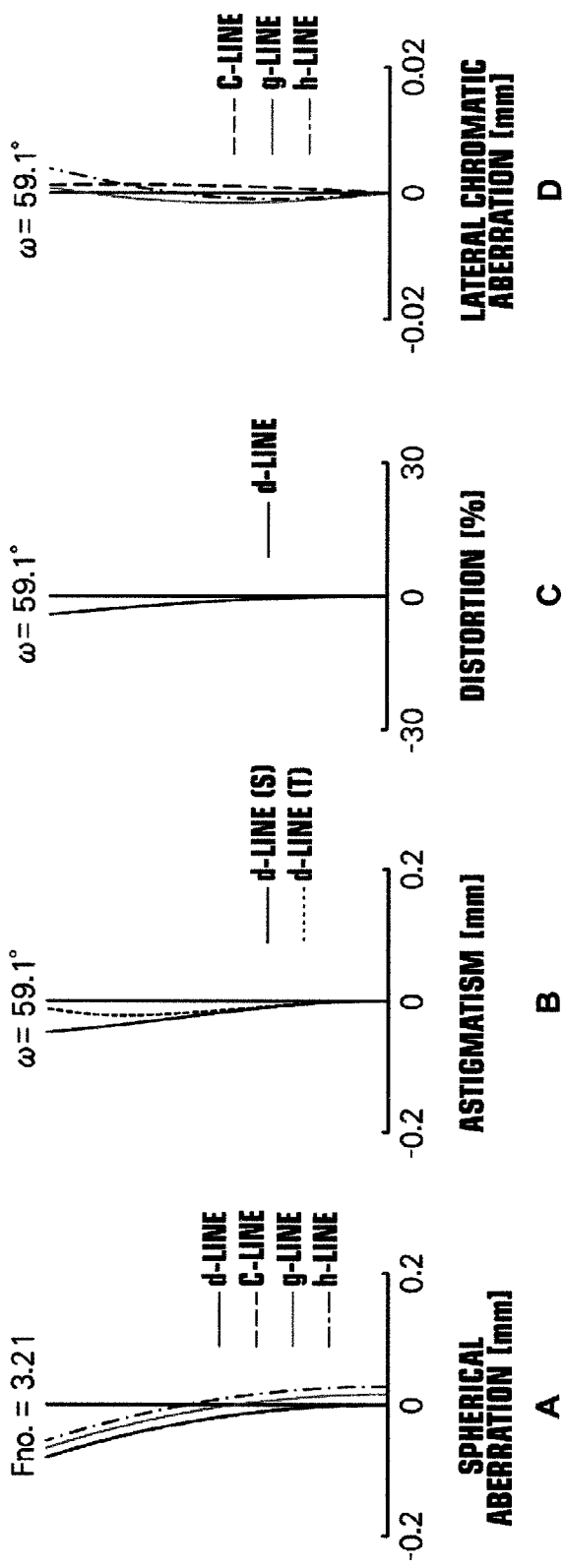

A to D of FIG. 11 show aberration diagrams of the endoscopic objective lens of Example 5 of the present invention.

Figure 12:
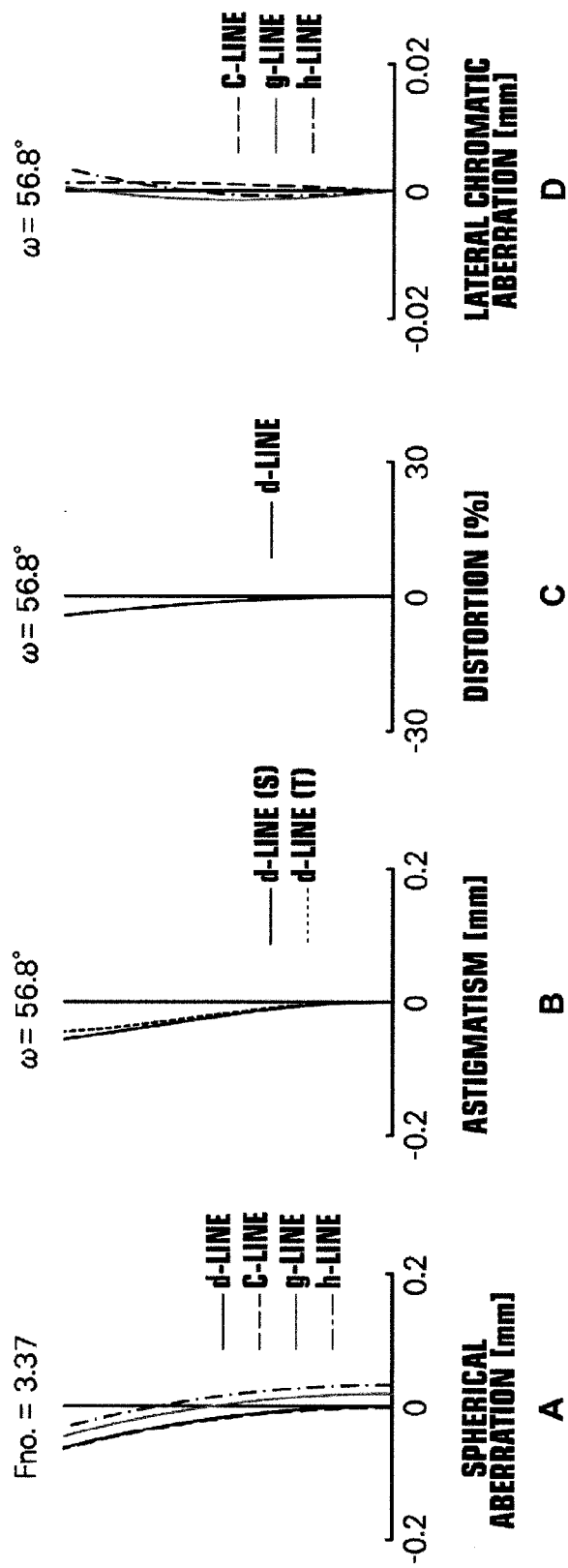

A to D of FIG. 12 show aberration diagrams of the endoscopic objective lens of Example 6 of the present invention.

Figure 13:
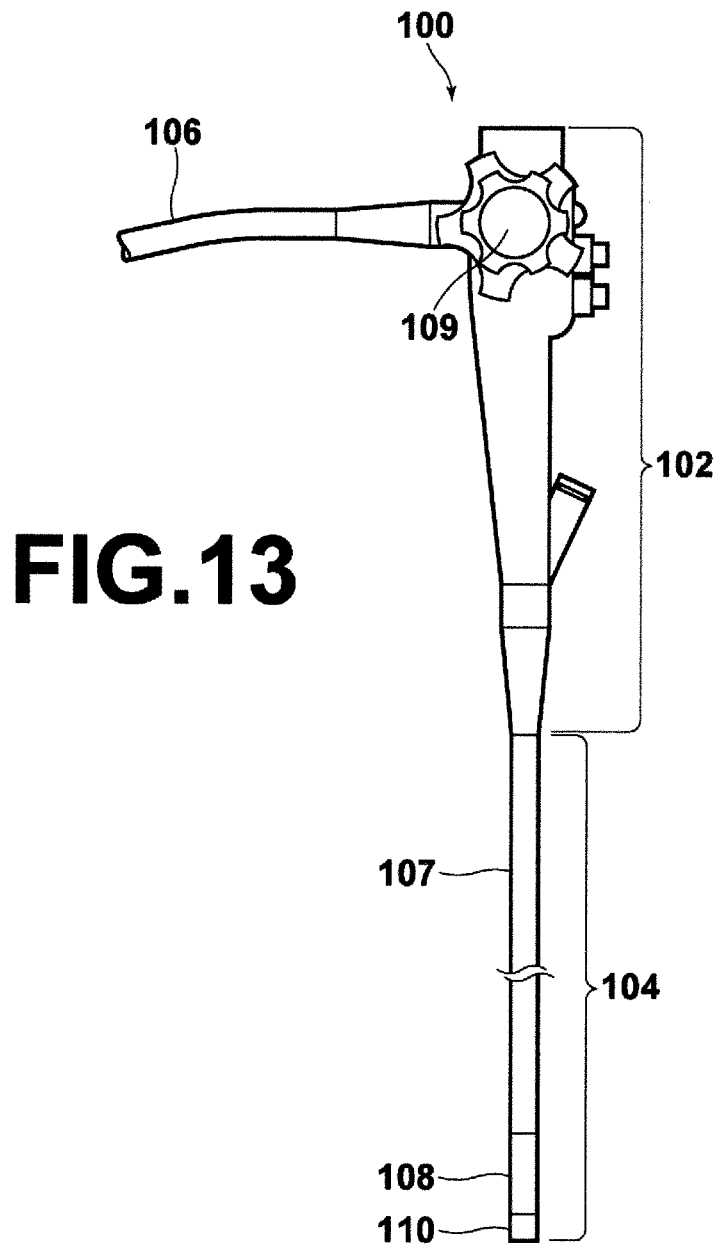

FIG. 13 illustrates a schematic view of an endoscope according to an embodiment of the present invention.

Figure 14:
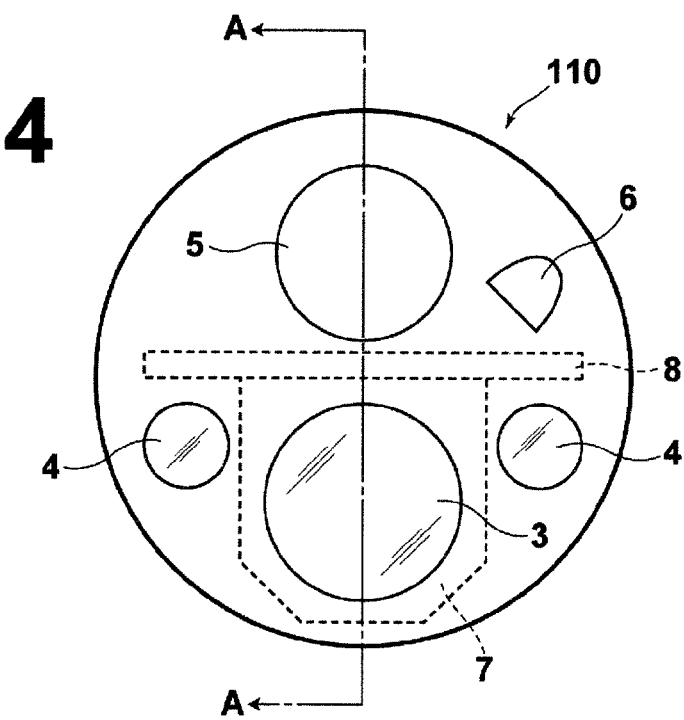

FIG. 14 is a plan view of a distal end face of an insertion section of the endoscope according to the embodiment of the present invention.

Figure 15:
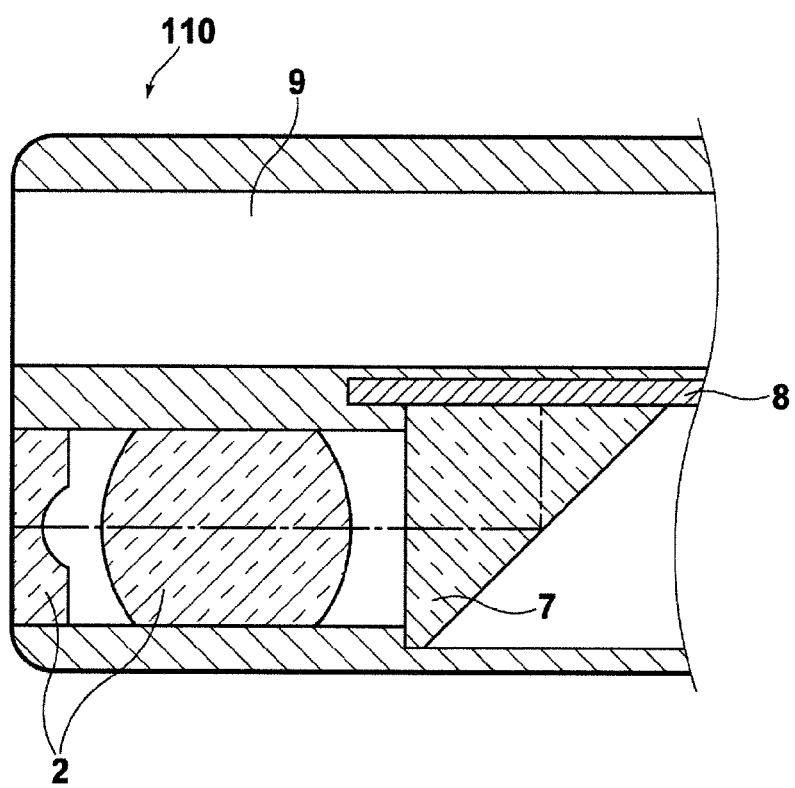

FIG. 15 is a cross-sectional view of a relevant part of the distal end section of the endoscope according to the embodiment of the present invention.

BEST MODE FOR CARRYING OUT THE INVENTION

Hereinafter, embodiments of the present invention will be described in detail with reference to the accompanying drawings. FIG. 1 illustrates the configuration of an endoscopic objective lens according to one embodiment of the present invention in cross-section that includes the optical axis Z. The configuration example illustrated in FIG. 1 corresponds to the lens configuration of Example 1, to be described later. Further, FIGS. 2 to 6 illustrate other configurations of endoscopic objective lenses according to embodiments of the present invention. The configuration examples illustrated in FIGS. 2 to 6 correspond to the lens configurations of Examples 2 to 6, to be described later. In FIG. 1, the left side is the object side and the right side is the image side, and the symbol Ri indicates a radius of curvature of $i^{th}$ surface in which a number i is given to each surface in a serially increasing manner toward the image side with the surface of the most object side constituent element being taken as the first surface. As the basic configurations and representation methods of the configuration examples of FIGS. 1 to 6 are identical, a description will be made, hereinafter, with reference to the configuration example shown in FIG. 1 as the representative.

The endoscopic objective lens of the present embodiment consists essentially of a first lens group G1 having a negative refractive power, an aperture stop St, and a second lens group G2 having a positive refractive power disposed in order from the object side along the optical axis Z. The first lens group G1 is composed of a cemented lens formed of a first lens L1 and a second lens L2 with a concave surface on the image side cemented in order from the object side. The second lens group G2 is composed of a positive single third lens L3 and a cemented lens formed of a fourth lens L4 and a fifth lens L5, either of the lenses being a positive lens and the other being a negative lens, and having a positive refractive power as a whole, disposed in order from the object side. The foregoing configuration is the basic configuration of the endoscopic objective lens of the present embodiment.

Note that the parallel plate optical member PP between the second lens group G2 and the image plane Sim assumes an optical path changing prism, a filter, a cover glass or the like. The use of the optical path changing prism will result in a folded optical path, but FIG. 1 illustrates a deployed optical path to facilitate understanding.

The refractive power arrangement of the negative lens group and the positive lens group in order from the object side causes the endoscopic objective lens of the present embodiment to be a retrofocus type lens system, thereby being capable of favorably conforming to a wide viewing angle required of endoscope. Further, the five lens configuration and the disposition of the cemented lenses on each of the object side and the image side of the aperture stop St allow satisfactory correction of chromatic aberration while downsizing the lens system by reducing the number of lenses as much as possible.

Formation of the first lens group G1 with only one cemented lens formed of two lenses allows longitudinal chromatic aberration to be corrected satisfactorily while reducing the number of lenses.

The cemented lens in the first lens group G1 may be a cemented lens formed of a first lens L1 having a positive refractive power and a second lens L2 having a negative refractive power or a cemented lens formed of a first lens L1 having a negative refractive power and a second lens L2 having a negative refractive power. If the first lens L1 is a positive lens, the second lens L2 is preferably a biconcave lens to secure a negative refractive power of the first lens group G1 to cause the lens system to be a wide angle optical system appropriate for endoscopes. If the first lens L1 is a negative lens, the second lens L2 may be a negative meniscus lens and doing so is advantageous for increasing the angle of view and achieving satisfactory aberration correction.

The object side surface of the first lens L1, which is located on the most object side of the entire system, is preferably a plane surface or a convex surface to prevent an attached substance, such as a liquid or the like, from remaining on the surface or to reduce the remaining amount when the endoscopic objective lens is installed in an endoscope and used.

The image side surface of the second lens L2 is formed in concave. In order to suppress the ray height at the first lens L1 for diameter reduction, the distance between the first lens group G1 and the aperture stop St is preferably reduced. But the reduction of the distance causes the angle formed by an off-axis light ray exiting from the image side surface of the second lens L2 toward the aperture stop St with the optical axis Z to be increased in a wide angle optical system like an endoscopic objective lens. Therefore, the image side lens surface of the second lens L2 is formed in concave to reduce the angle of refraction of a light ray on the surface in comparison with the case in which the lens surface is formed in convex or plane, whereby aberration generated on the surface can be reduced.

From the foregoing circumstances, the first lens group G1 may employ a configuration composed of a cemented lens of a plano-convex first lens L1 and a biconcave second lens L2, a cemented lens of a plano-concave first lens L1 and a negative meniscus second lens L2 with a convex surface on the object side, a cemented lens of a negative meniscus first lens L1 with a convex surface on the object side and a negative meniscus second lens L2 with a convex surface on the object side, or the like.

The third lens L3 is the lens disposed following the negative first lens group G1 and the aperture stop St, and by giving a positive refractive power to this lens, light rays may be guided to the image plane Sim while securing a long back focus sufficient to dispose an optical path changing prism.

For example, the third lens L3 may be a positive meniscus lens with a concave surface of the object side, and doing so allows the amount of aberration generated on the object side surface of the third lens L3 to be reduced in comparison with the case in which the object side surface of the third lens L3 is formed in convex or plane.

The second lens group G2 may correct chromatic aberration satisfactorily by having a cemented lens formed of a positive lens and a negative lens.

As the cemented lens in the second lens group G2, FIG. 1 illustrates an example in which a fourth lens L4 having a positive refractive power and a fifth lens L5 having a negative refractive power are cemented in order from the object side. Alternatively, a configuration may be adopted in which a fourth lens L4 having a negative refractive power and a fifth lens L5 having a positive refractive power are cemented in order from the object side.

When considering a light beam propagating toward the image side, if the cemented lens in the second lens group G2 is formed of a negative lens and a positive lens cemented in order from the object side, however, the light beam diverged by the negative lens is incident on the positive lens in the cemented lens and the ray height at the positive lens is increased in comparison with the configuration in which the order of the negative lens and the positive lens is reversed, whereby the outer diameter of the lens is increased, which is disadvantageous for diameter reduction.

Further, in the configuration in which the cemented lens in the second lens group G2 is formed of a negative lens and a positive lens cemented in order from the object side, the positive lens is located further on the image side and the ray height at the positive lens is increased in comparison with the configuration in which the order of the negative lens and the positive lens is reversed, whereby the outer diameter of the lens is increased, which is disadvantageous for diameter reduction. Further, for positive lenses, the rim thickness (edge thickness) is generally reduced as the outer diameter is increased. Therefore, the center thickness may possibly need to be increased to secure the rim thickness, which may also be a concern for achieving the downsizing in the optical axis direction.

From the foregoing circumstances, it is advantageous for implementing downsizing and diameter reduction to arrange a positive lens and a negative lens in order from the object side for the cemented lens in the second lens group G2, as illustrated in FIG. 1. More specifically, the cemented lens in the second lens group G2 may be, for example, formed of a biconvex fourth lens L4 and a negative meniscus fifth lens L5 with a convex surface on the image side.

Further, the endoscopic objective lens of the present embodiment preferably satisfies any one or any combination of conditional expressions (1) to (9) given below.

$$25 < vd2 - vd1 < 60 \quad (1)$$

$$-1.6 < (R3+R2)/(R3-R2) < -0.5 \quad (2)$$

$$1 < |R2/R3| < 30 \quad (3)$$

$$0.40 < |DS \times fG1/(f \times (DS - fG1))| < 0.60 \quad (4)$$

$$|D1/R2| < 0.10 \quad (5)$$

$$0.80 < Bf/f < 1.38 \quad (6)$$

$$20 < vdp - vdn < 40 \quad (7)$$

$$1.85 < Nd1 < 1.92 \quad (8)$$

$$35 < vd1 < 45 \quad (9)$$

where vd1: Abbe number of the first lens with respect to the d-line, vd2: Abbe number of the second lens with respect to the d-line, R2: radius of curvature of the object side surface of the second lens, R3: radius of curvature of the image side surface of the second lens, DS: distance on the optical axis from the object side surface of the first lens to the stop, fG1: focal length of the first lens group, f: focal length of the entire system, D1: center thickness of the first lens, Bf back focus of the entire system, vdp: Abbe number of the positive lens of the cemented lens in the second lens group with respect to the d-line, vdn: Abbe number of the negative lens of the cemented lens in the second lens group with respect to the d-line, and Nd1: refractive index of the first lens with respect to the d-line.

The operational effects of the foregoing conditional expressions will be described. The conditional expression (1) relates to the difference in Abbe number between the two lenses of the cemented lens disposed immediately before the object side of the aperture stop St. As the configuration at a low ray height portion near the aperture stop St has a large influence on longitudinal chromatic aberration, it is preferable that the Abbe number of the constituent material of the portion is adjusted by the cemented lens near the aperture stop St. If the lens system reaches or exceeds the upper limit of the conditional expression (1), longitudinal chromatic aberration is under-corrected. If the lens system falls to or below lower limit of the conditional expression (1), longitudinal chromatic aberration is over-corrected. Satisfaction of the conditional expression (1) allows longitudinal chromatic aberration to be corrected satisfactorily. In order to further enhance the foregoing effects, the lens system more preferably satisfies a conditional expression (1') given below and further preferably satisfies a conditional expression (1") given below:

$$27 < vd2 - vd1 < 58 \quad (1')$$

$$29 < vd2 - vd1 < 55 \quad (1'')$$

Satisfaction of the conditional expression (1) allows the use of a material in the region of low dispersion materials for the second lens L2, whereby chromatic aberration may be corrected optimally. Further, the increase in the difference between the Abbe numbers of the two lenses of the cemented lens in the first lens group G1 within the range that satisfies the conditional expression (1) allows the absolute value of the radius of curvature of the cemented surface of the cemented lens to be increased. In a case in which the first lens group G1 has a positive lens, a larger absolute value of the radius of curvature of the cemented surface may more reduce the need to increase the center thickness of the positive lens in the first lens group G1 in order to secure the rim thickness (edge thickness) of the positive lens. Therefore, satisfaction of the conditional expression (1) may contribute to the reduction of the first lens group G1 in the optical axis direction.

The conditional expression (2) relates to the shape of the second lens L2. It also relates to the shapes of the cemented surface of the first lens group G1 and the most image side surface in the first lens group G1. If the lens system reaches or exceeds the upper limit of the conditional expression (2), the longitudinal chromatic aberration is over-corrected and lateral chromatic aberration is under-corrected. If the lens system falls to or below the lower limit of the conditional expression (2), the longitudinal chromatic aberration is under-corrected and lateral chromatic aberration is over-corrected. Satisfaction of the conditional expression (2) allows chromatic aberration to be corrected satisfactorily. In order to further enhance the foregoing effects, the lens system more preferably satisfies a conditional expression (2') given below and further preferably satisfies a conditional expression (2") given below:

$$-1.5<(R3+R2)/(R3-R2)<-0.6 \quad (2')$$

$$-1.4<(R3+R2)/(R3-R2)<-0.7 \quad (2'')$$

Further, satisfaction of the conditional expression (2) allows the absolute value of the radius of curvature of the most image side surface in the first lens group G1 to be made smaller than the absolute value of the radius of curvature of the cemented surface, while using a biconcave lens or a negative meniscus lens with a concave surface on the image side as the second lens L2. This allows the distance between the first lens group G1 and the aperture stop St to be reduced. The reduction in the distance allows the ray height at the first lens group G1 to be reduced, which is advantageous for diameter reduction.

The conditional expression (3) also relates to the shape of the second lens L2, and also relates to the shapes of the cemented surface of the first lens group G1 and the most image side surface in the first lens group G1. If the lens system reaches or exceeds the upper limit of the conditional expression (3), the longitudinal chromatic aberration is over-corrected, lateral chromatic aberration is under-corrected, and field curvature is generated, whereby the field curvature tends to become over. If the lens system falls to or below the lower limit of the conditional expression (3), the longitudinal chromatic aberration is under-corrected, lateral chromatic aberration is over-corrected, and field curvature is generated, whereby the field curvature tends to become under. Satisfaction of the conditional expression (3) allows chromatic aberration and field curvature to be corrected satisfactorily. In order to further enhance the foregoing effects, the lens system more preferably satisfies a conditional expression (3') given below and further preferably satisfies a conditional expression (3") given below:

$$3<|R2/R3|<25 \quad (3')$$

$$6<|R2/R3|<20 \quad (3'')$$

Further, satisfaction of the conditional expression (3) allows the absolute value of the radius of curvature of the most image side surface in the first lens group G1 to be made smaller than the absolute value of the radius of curvature of the cemented surface in the first lens group G1, which is advantageous for diameter reduction, as in the conditional expression (2) described above.

The conditional expression (4) relates to entrance pupil position. If the lens system reaches or exceeds the upper limit of the conditional expression (4), the distance from the object side surface of the first lens L1 to the entrance pupil position is increased and the outer diameter of the first lens L1 is increased. If the lens system falls to or below the upper limit of the conditional expression (4), the angle of view is reduced, whereby a wide angle configuration required of endoscopic object lens cannot be realized. Satisfaction of the conditional expression (4) allows the diameter reduction and the wide angle configuration required of endoscopic objective lens to be realized. In order to further enhance the foregoing effects, the lens system more preferably satisfies a conditional expression (4') given below and further preferably satisfies a conditional expression (4") given below:

$$0.45<|DS \times fG1/(fx(DS-fG1))|<0.55 \quad (4')$$

$$0.48<|DS \times fG1/(fx(DS-fG1))|<0.53 \quad (4'')$$

The conditional expression (5) relates to the axial thickness of the first lens L1 and the radius of curvature of the image side surface of the first lens L1. If the lens system reaches or exceeds the upper limit of the conditional expression (5), the overall length of the lens system is increased and the outer diameter of the first lens L1 is increased, which contradicts to downsizing and diameter reduction. Satisfaction of the conditional expression (5) may contribute to downsizing and diameter reduction.

The values corresponding to the conditional expression (5) more preferably satisfy a conditional expression (5') given below and further preferably satisfy a conditional expression (5") given below.

$$0.01<|D1/R2|<0.08 \quad (5')$$

$$0.025 \le |D1/R2|1<0.07 \quad (5'')$$

Satisfaction of the upper limit of the conditional expression (5') may further contribute to downsizing and diameter reduction in comparison with the case in which the upper limit of the conditional expression (5) is satisfied. If the lens system falls to the lower limit of the conditional expression (5'), longitudinal chromatic aberration is difficult to be corrected sufficiently. Satisfaction of the conditional expression (5') is advantageous for downsizing, diameter reduction, and longitudinal chromatic aberration correction. Satisfaction of the conditional expression (5") may further enhance these effects.

The conditional expression (6) relates to the back focus ratio. If the lens system reaches or exceeds the upper limit of the conditional expression (6), the overall length of the lens system is increased. If the lens system falls to or below the lower limit of the conditional expression (6), disposition of an optical path changing prism or the like is difficult. Satisfaction of the conditional expression (6) allows a sufficient back focus to dispose an optical path changing prism or the like to be secured, while achieving downsizing. In order to further enhance the foregoing effects, the lens system more preferably satisfies a conditional expression (6') given below and further preferably satisfies a conditional expression (6") given below:

$$1.00<Bf/f<1.37 \quad (6')$$

$$1.20<Bf/f<1.35 \quad (6'')$$

The conditional expression (7) relates to the difference in Abbe number between the positive lens and the negative lens of the cemented lens in the second lens group G2. As the configuration at a high ray height portion remote from the aperture stop St has a large influence on lateral chromatic aberration, it is preferable that the Abbe number of the constituent material of the portion is adjusted by the cemented lens remote from the aperture stop St. If the lens system reaches or exceeds the upper limit of the conditional expression (7), the lateral chromatic aberration is over-corrected. If the lens system falls to or below the lower limit of the conditional expression (7), the lateral chromatic aberration is under-corrected. Satisfaction of the conditional expression (7) allows lateral chromatic aberration to be corrected satisfactorily. In order to further enhance the foregoing effects, the lens system more preferably satisfies a conditional expression (7') given below and further preferably satisfies a conditional expression (7") given below:

$$22<\nu dp-\nu dn<38 \tag{7'}$$

$$23<\nu dp-\nu dn<36 \tag{7''}$$

The conditional expression (8) relates to the refractive index of the first lens L1. As the first lens L1 is the lens disposed on the most object side in the endoscopic object lens, the material of the lens may sometimes be required to have biocompatibility. Further, roughly speaking, the currently available optical materials tend to decrease in Abbe number with increase in refractive index. If the lens system reaches or exceeds the upper limit of the conditional expression (8), the attempt to correct various types of aberration using a material which has biocompatibility and can be used as an optical material may result in reduced material selectivity and the various types of aberrations cannot be corrected sufficiently. If the lens system falls to or below the lower limit of the conditional expression (8), a wide angle configuration required of endoscopic object lens is difficult to be realized. Satisfaction of the conditional expression (8) allows a wide angle configuration to be realized while using a good biocompatible material and correcting aberrations satisfactorily. In order to further enhance the foregoing effects, the lens system more preferably satisfies a conditional expression (8') given below and further preferably satisfies a conditional expression (8") given below:

$$1.86<Nd1<1.90 \tag{8'}$$

$$1.88<Nd1<1.89 \tag{8''}$$

The conditional expression (9) relates to the Abbe number of the first lens L1. If the lens system reaches or exceeds the upper limit of the conditional expression (9), longitudinal chromatic aberration is over-corrected. If the lens system falls to or below the lower limit of the conditional expression (9), chromatic dispersion cannot be suppressed and a considerable amount of chromatic aberration is generated. Satisfaction of the conditional expression (9) allows chromatic aberration to be corrected satisfactorily. In order to further enhance the foregoing effects, the lens system more preferably satisfies a conditional expression (9') given below and further preferably satisfies a conditional expression (9") given below:

$$38<\nu d1<43 \tag{9'}$$

$$40<\nu d1<42 \tag{9''}$$

Satisfaction of the conditional expressions (8) and (9) simultaneously allows various types of aberrations, in particular, chromatic aberration to be corrected satisfactorily, while using a good biocompatible material and achieving a wide angle configuration.

The foregoing preferable configurations and conditional expressions may be selected, as appropriate, according to the requirements of the endoscopic objective lens. For example, the following two aspects may be cited as preferable examples.

The first aspect has the basic configuration described above and satisfies the conditional expressions (1) and (2). The second aspect has the basic configuration described above and satisfies the conditional expressions (3) and (4).

Note that the first aspect may be configured to satisfy, in addition to the conditional expressions (1) and (2), the foregoing conditional expressions other than the conditional expressions (1) and (2), and the second aspect may be configured to satisfy, in addition to the conditional expressions (3) and (4), the foregoing conditional expressions other than the conditional expressions (3) and (4).

If the endoscopic objective lens is installed in an endoscope without any protection material, the most object side lens will be exposed to body fluid, cleaning liquid, direct sunlight, grease and the like. Therefore, a material which is highly resistant to water, weather, acid, chemical, and the like is preferably used for this lens. For example, a material ranked in class 1 for weight loss rate in the powder test for resistance to water and acid and ranked in class 1 in the surface test for resistance to weather defined by Japan Optical Glass Manufacturers' Association is preferably used.

Next, numerical examples of the endoscopic objective lens of the present invention will be described.

Example 1

The lens configuration diagram of the endoscopic objective lens of Example 1 is as illustrated in FIG. 1 and, therefore, duplicated description will be omitted here.

The endoscopic objective lens of Example 1 has the following schematic configuration. The endoscopic objective lens of Example 1 consists of a first lens group G1 having a negative refractive power, an aperture stop St, and a second lens group G2 having a positive refractive power, disposed in order from the object side. The first lens group G1 is composed of a first lens L1, which is a plano-convex lens with its plane surface on the object side, and a second lens L2, which is a biconcave lens, disposed in order from the object side. The first lens L1 and the second lens L2 are cemented. The second lens group G2 is composed of a third lens L3, which is a positive meniscus lens with a convex surface on the image side, a fourth lens L4, which is a biconvex lens, and a fifth lens L5 with a concave surface on the object side, disposed in order from the object side. The third lens L3 is a single lens, not cemented. The fourth lens L4 and the fifth lens L5 are cemented. The first lens L1 to fifth lens L5 are all spherical lenses.

The lens data and specs of the endoscopic objective lens of Example 1 are shown in Table 1. The Si column in the basic lens data table indicates the $i^{th}$ surface number in which a number i (i=1, 2, 3, - - - ) is given to each surface in a serially increasing manner toward the image side with the object side surface of the most object side constituent element being taken as the first surface. The Ri column indicates the radius of curvature of the $i^{th}$ surface and the Di column indicates the surface distance on the optical axis Z between the $i^{th}$ surface and the $(i+1)^{th}$ surface. The Ndj column indicates the refractive index of the $j^{th}$ optical element with respect to the d-line (wavelength of 587.56 nm) in which a number j (j=1, 2, 3, - - - ) is given to each optical element in a serially increasing manner toward the image side with the most object side optical element being taken as the first element, and the vdj column indicates the Abbe number of the $j^{th}$ optical element with respect to the d-line.

The sign of the radius of curvature is positive if the surface shape is convex on the object side and negative if it is convex on the image side. The value at the bottom of the surface distance column indicates the surface distance on the optical axis Z between the most image side surface in the table and the image plane. Note that the aperture stop St and the optical member PP are also included in the basic lens data, and the surface number column corresponding to the aperture stop St includes the word (St) in addition to the surface number.

The values in the table of specs are those with respect to the d-line. The table of specs indicates values of focal length f, back focus Bf, F-number Fno. and total angle of view 2ω (unit: degree).

In Table 1, "mm" is used as the unit of lengths. But, this is only an example and other appropriate units may also be used, as optical systems can be used by proportionally enlarged or reduced. Further, Table 1 indicates values rounded to a predetermined digit. The values in the basic lens data of Table 1 are those when the object distance (distance from the object side surface of the first lens L1 to the object) is 8.76 mm.

TABLE 1

Example 1

Basic Lens Data

| Si | Ri | Di | Ndj | ν dj | Specs (d-line) | |
|---|---|---|---|---|---|---|
| 1 | ∞ | 0.29 | 1.88299 | 40.80 | f | 1.0078 |
| 2 | −8.5932 | 0.29 | 1.43875 | 94.93 | Bf | 1.3352 |
| 3 | 0.5537 | 0.19 | | | Fno. | 3.24 |
| 4(St) | ∞ | 0.04 | | | 2 ω [°] | 115.8 |
| 5 | −2.2260 | 0.82 | 1.65160 | 58.55 | | |
| 6 | −0.7387 | 0.15 | | | | |
| 7 | 5.5249 | 0.73 | 1.72916 | 54.68 | | |
| 8 | −0.9407 | 0.29 | 2.00272 | 19.32 | | |
| 9 | −1.7629 | 0.30 | | | | |
| 10 | ∞ | 2.12 | 1.88299 | 40.80 | | |
| 11 | ∞ | 0.01 | | | | |

The aberration diagrams of spherical aberration, astigmatism, distortion and lateral chromatic aberration of the endoscopic objective lens of Example 1 are shown in A to D of FIG. 7 respectively. Each of the aberration diagrams of spherical aberration, astigmatism and distortion shows aberration with the d-line as the reference wavelength, but the spherical aberration diagram also shows aberrations with respect to the C-line (wavelength 656.27 nm), the g-line (wavelength 435.84 nm) and the h-line (wavelength 404.66 nm). In the astigmatism aberration diagram, aberrations in the sagittal direction and the tangential direction are illustrated by the solid line and the broken line respectively. The lateral chromatic aberration diagram shows aberrations with respect to the C-line, the g-line and the h-line. The "Fno." in the spherical aberration diagram represents F-number, and "ω" in other aberration diagrams represents the half angle of view. The aberration diagrams shown in A to D of FIG. 7 are those when the object distance is 8.76 mm.

The illustration method, and the symbols in each type of data, their meaning, representation method, and the like described in Example 1 are applied also to the following examples unless otherwise specifically described, and duplicated description will be omitted herein below.

Example 2

The lens configuration diagram of the endoscopic objective lens of Example 2 is as illustrated in FIG. 2. The endoscopic objective lens of Example 2 has a lens configuration almost the same as that of Example 1. The lens data and specs of the endoscopic objective lens of Example 2 are shown in Table 2. The aberration diagrams of spherical aberration, astigmatism, distortion and lateral chromatic aberration of the endoscopic objective lens of Example 2 are shown in A to D of FIG. 8 respectively. The values of basic lens data in Table 2 and the aberration diagrams shown in A to D of FIG. 8 are those when the object distance is 8.78 mm.

TABLE 2

Example 2

Basic Lens Data

| Si | Ri | Di | Ndj | ν dj | Specs (d-line) | |
|---|---|---|---|---|---|---|
| 1 | ∞ | 0.29 | 1.88299 | 40.80 | f | 0.9966 |
| 2 | −4.8793 | 0.29 | 1.49700 | 81.54 | Bf | 1.3166 |
| 3 | 0.7216 | 0.18 | | | Fno. | 3.06 |
| 4(St) | ∞ | 0.03 | | | 2 ω [°] | 116.8 |
| 5 | −2.5011 | 1.09 | 1.75500 | 52.32 | | |
| 6 | −0.8846 | 0.15 | | | | |
| 7 | 13.8783 | 0.73 | 1.83481 | 42.73 | | |
| 8 | −0.9427 | 0.29 | 2.00272 | 19.32 | | |
| 9 | −2.0629 | 0.28 | | | | |
| 10 | ∞ | 2.12 | 1.88299 | 40.80 | | |
| 11 | ∞ | 0.00 | | | | |

Example 3

The lens configuration diagram of the endoscopic objective lens of Example 3 is as illustrated in FIG. 3. The endoscopic objective lens of Example 3 has a lens configuration almost the same as that of Example 1. The lens data and specs of the endoscopic objective lens of Example 3 are shown in Table 3. The aberration diagrams of spherical aberration, astigmatism, distortion and lateral chromatic aberration of the endoscopic objective lens of Example 3 are shown in A to D of FIG. 9 respectively. The values of basic lens data in Table 3 and the aberration diagrams shown in A to D of FIG. 9 are those when the object distance is 8.65 mm.

TABLE 3

Example 3

Basic Lens Data

| Si | Ri | Di | Ndj | ν dj | Specs (d-line) | |
|---|---|---|---|---|---|---|
| 1 | ∞ | 0.29 | 1.88299 | 40.80 | f | 1.0067 |
| 2 | −14.4187 | 0.29 | 1.48749 | 70.23 | Bf | 1.2913 |
| 3 | 0.7365 | 0.17 | | | Fno. | 3.17 |
| 4(St) | ∞ | 0.04 | | | 2 ω [°] | 113.0 |
| 5 | −3.7132 | 1.10 | 1.74100 | 52.64 | | |
| 6 | −0.8886 | 0.14 | | | | |
| 7 | 12.3234 | 0.72 | 1.83481 | 42.73 | | |
| 8 | −0.9285 | 0.29 | 2.00272 | 19.32 | | |
| 9 | −2.1694 | 0.27 | | | | |
| 10 | ∞ | 2.09 | 1.88299 | 40.80 | | |
| 11 | ∞ | 0.01 | | | | |

Example 4

The lens configuration diagram of the endoscopic objective lens of Example 4 is as illustrated in FIG. 4. The endoscopic objective lens of Example 4 has a lens configuration almost the same as that of Example 1, but differs in that the first lens L1 is a plano-concave lens with its plane surface on the object side. The lens data and specs of the endoscopic objective lens of Example 4 are shown in Table 4. The aberration diagrams of spherical aberration, astigmatism, distortion and lateral chromatic aberration of the endoscopic objective lens of Example 4 are shown in A to D of FIG. 10 respectively. The values of basic lens data in Table 4 and the aberration diagrams shown in A to D of FIG. 10 are those when the object distance is 8.67 mm.

TABLE 4

Example 4

Basic Lens Data

| Si | Ri | Di | Ndj | ν dj | Specs (d-line) | |
|---|---|---|---|---|---|---|
| 1 | ∞ | 0.29 | 1.88299 | 40.80 | f | 1.0059 |
| 2 | 4.8189 | 0.29 | 1.48749 | 70.23 | Bf | 1.2459 |
| 3 | 0.7491 | 0.19 | | | Fno. | 3.35 |
| 4(St) | ∞ | 0.00 | | | 2 ω [°] | 114.4 |
| 5 | −26.5409 | 1.14 | 1.74100 | 52.64 | | |
| 6 | −0.9246 | 0.14 | | | | |
| 7 | 8.6713 | 0.72 | 1.83481 | 42.73 | | |
| 8 | −0.9310 | 0.29 | 2.00272 | 19.32 | | |
| 9 | −2.3960 | 0.22 | | | | |
| 10 | ∞ | 2.10 | 1.88299 | 40.80 | | |
| 11 | ∞ | 0.01 | | | | |

Example 5

The lens configuration diagram of the endoscopic objective lens of Example 5 is as illustrated in FIG. 5. The endoscopic objective lens of Example 5 has a lens configuration almost the same as that of Example 1, but differs in that each of the first lens L1 and the second lens L2 is a negative meniscus lens with a concave surface on the image side. The lens data and specs of the endoscopic objective lens of Example 5 are shown in Table 5. The aberration diagrams of spherical aberration, astigmatism, distortion and lateral chromatic aberration of the endoscopic objective lens of Example 5 are shown in A to D of FIG. 11 respectively. The values of basic lens data in Table 5 and the aberration diagrams shown in A to D of FIG. 11 are those when the object distance is 8.83 mm.

TABLE 5

Example 5

Basic Lens Data

| Si | Ri | Di | Ndj | ν dj | Specs (d-line) | |
|---|---|---|---|---|---|---|
| 1 | 49.0707 | 0.29 | 1.88299 | 40.80 | f | 1.0006 |
| 2 | 5.6821 | 0.29 | 1.49700 | 81.54 | Bf | 1.2544 |
| 3 | 0.8153 | 0.20 | | | Fno. | 3.21 |
| 4(St) | ∞ | 0.00 | | | 2 ω [°] | 118.2 |
| 5 | −5.9257 | 1.19 | 1.75500 | 52.32 | | |

TABLE 5-continued

Example 5

Basic Lens Data

| Si | Ri | Di | Ndj | ν dj | Specs (d-line) |
|---|---|---|---|---|---|
| 6 | −0.9283 | 0.15 | | | |
| 7 | 9.8659 | 0.74 | 1.83481 | 42.73 | |
| 8 | −0.9477 | 0.29 | 2.00272 | 19.32 | |
| 9 | −2.3555 | 0.21 | | | |
| 10 | ∞ | 2.13 | 1.88299 | 40.80 | |
| 11 | ∞ | 0.01 | | | |

Example 6

The lens configuration diagram of the endoscopic objective lens of Example 6 is as illustrated in FIG. 6. The endoscopic objective lens of Example 6 has a lens configuration almost the same as that of Example 4. The lens data and specs of the endoscopic objective lens of Example 6 are shown in Table 6. The aberration diagrams of spherical aberration, astigmatism, distortion and lateral chromatic aberration of the endoscopic objective lens of Example 6 are shown in A to D of FIG. 12 respectively. The values of basic lens data in Table 6 and the aberration diagrams shown in A to D of FIG. 12 are those when the object distance is 8.62 mm.

TABLE 6

Example 6

Basic Lens Data

| Si | Ri | Di | Ndj | ν dj | Specs (d-line) | |
|---|---|---|---|---|---|---|
| 1 | ∞ | 0.29 | 1.88299 | 40.80 | f | 1.0038 |
| 2 | 4.7887 | 0.29 | 1.48749 | 70.23 | Bf | 1.2447 |
| 3 | 0.7497 | 0.19 | | | Fno. | 3.37 |
| 4(St) | ∞ | 0.00 | | | 2 ω [°] | 113.6 |
| 5 | −25.2689 | 1.14 | 1.74100 | 52 64 | | |
| 6 | −0.9201 | 0.14 | | | | |
| 7 | 9.1017 | 0.72 | 1.83481 | 42.73 | | |
| 8 | −0.9252 | 0.29 | 2.00272 | 19.32 | | |
| 9 | −2.3753 | 0.23 | | | | |
| 10 | ∞ | 2.08 | 1.88299 | 40.80 | | |
| 11 | ∞ | 0.01 | | | | |

Table 7 summarizes values corresponding to the aforementioned conditional expressions (1) to (7) and a value of focal length fG1 of the first lens group G1, which is a value related to the conditional expression (4), for each of Examples 1 to 6. The values shown in Table 7 are those with respect to the d-line.

TABLE 7

| Expression No. | | Example 1 | Example 2 | Example 3 | Example 4 | Example 5 | Example 6 |
|---|---|---|---|---|---|---|---|
| (1) | ν d2 − ν d1 | 54.13 | 40.74 | 29.43 | 29.43 | 40.74 | 29.43 |
| (2) | (R3 + R2)/(R3 − R2) | −1.14 | −1.35 | −1.11 | −0.73 | −0.75 | −0.73 |
| (3) | |R2/R3| | 15.5 | 6.8 | 19.6 | 6.4 | 7.0 | 6.4 |
| (4) | |DS × fG1/(f × (DS − fG1))| | 0.489 | 0.524 | 0.506 | 0.499 | 0.525 | 0.500 |
| | fG1 | −1.3653 | −1.6692 | −1.5850 | −1.3454 | −1.5071 | −1.3453 |
| (5) | |D1/R2| | 0.034 | 0.059 | 0.020 | 0.060 | 0.051 | 0.061 |
| (6) | Bf/f | 1.325 | 1.321 | 1.283 | 1.239 | 1.254 | 1.240 |
| (7) | ν dp − ν dn | 35.36 | 23.41 | 23.41 | 23.41 | 23.41 | 23.41 |

Next, an embodiment of an endoscope to which the endoscopic objective lens of the present invention is applied will be described with reference to FIGS. 13 to 15. FIG. 13 is a schematic overall configuration diagram of the endoscope. The endoscope 100 shown in FIG. 13 basically includes an operation section 102, an insertion section 104 and a connector section (not shown) for pulling out a universal cord 106. The insertion section 104 to be inserted into a body of a patient is coupled to the distal end side of the operation section 102 and the universal code 106 to be connected to the connector section for connecting to a light source and the like is drawn out from the proximal end side of the operation section 102.

The most part of the insertion section 104 is a soft portion 107 that can be bent in an arbitrary direction along an insertion path and a bending portion 108 is coupled to the tip of the soft portion 107 and then a distal end portion 110 is coupled to the tip of the bending portion 108. The bending portion 108 is provided for directing the distal end portion 110 to a desired direction, and a bending operation can be performed by turning a bending operation knob 109 provided on the operation section 102.

FIG. 14 is a plan view of the tip of the distal end portion 110 in a plane perpendicular to a long axis direction of the insertion section 104. FIG. 15 is a cross-sectional view of a relevant part of the distal end portion 110 taken along the line A-A in FIG. 14. As illustrated in FIG. 14, the distal end surface of the distal end portion 110 includes an observation window 3 which is the outer surface of the endoscopic objective lens 2, two illumination windows 4, disposed on both sides of the observation window 3, for projecting illumination light, a treatment tool insertion opening 5 and an air•water feed nozzle 6.

As illustrated in FIG. 15, the distal end portion 110 further includes inside therein the endoscopic objective lens 2 whose optical axis is disposed in parallel to a long axis direction of the insertion section 104, an optical path changing prism 7 for bending the optical path on the image side of the endoscopic objective lens 2 about 90 degrees and a solid-state image sensor 8 cemented to the optical path changing prism 7 such that the light receiving surface thereof is in parallel to the long axis direction of the insertion section 104.

Note that the endoscopic objective lens 2 is depicted conceptually in FIG. 15. The solid-state image sensor 8 is disposed such that the imaging surface thereof corresponds to the image plane of the endoscopic objective lens 2 and is provided to output an electrical signal by capturing an optical image formed by the endoscopic objective lens 2. The solid-state image sensor 8 includes a cover glass for protecting the light receiving surface, and those shown as the solid-state image sensors 8 in FIGS. 14 and 15 include cover glasses. In FIG. 15, the optical axis of the observation optical system formed of the endoscopic objective lens 2 is shown by the dash-dot line. Employment of the configuration in which the optical path is folded as illustrated in FIG. 15 allows a direct view observation optical system to be formed at the lower half of the distal end portion 110 and a treatment tool channel 9 to be formed at the upper half of the distal end portion 110, whereby many elements can be disposed in a small-diameter insertion section, as shown in FIG. 14.

So far, the present invention has been described by way of embodiments and Examples, but it should be understood that the present invention is not limited to the embodiments and Examples described above, and various changes and modifications may be made. For example, values of radius of curvature, surface distance, refractive index, Abbe number of each lens and the like are not limited to those shown in each Numerical Example and may take other values.

For example, each of the endoscopic objective lenses if the foregoing Examples is formed of refractive lenses without using any aspherical surface, but the endoscopic objective lens of the present invention is not limited to this. The endoscopic objective lens of the present may have a configuration in which chromatic aberration and other aberrations are corrected using not only the spherical refractive lenses but also either one or any combination of aspherical lens and GRIN (Gradient Index) lens.

What is claimed is:

1. An endoscopic objective lens, consisting essentially of a first lens group having a negative refractive power, a stop, and a second lens group having a positive refractive power, disposed in order from the object side, wherein:

the first lens group is composed of a cemented lens formed of a first lens and a second lens with a concave surface on the image side cemented in order from the object side;

the second lens group is composed of a positive single third lens and a cemented lens formed of a fourth lens and a fifth lens, either of which being a positive lens and the other being a negative lens, and having a positive refractive power as a whole, disposed in order from the object side; and the endoscopic objective lens satisfies conditional expressions (1') and (2) given below:

$$27<vd2-vd1<58 \qquad (1')$$

$$-1.6<(R3+R2)/(R3-R2)<-0.5 \qquad (2)$$

where
vd1: Abbe number of the first lens with respect to the d-line,
vd2: Abbe number of the second lens with respect to the d-line,
R2: radius of curvature of the object side surface of the second lens, and
R3: radius of curvature of the image side surface of the second lens.

2. The endoscopic objective lens as claimed in claim 1, wherein the endoscopic objective lens satisfies a conditional expression (2') given below:

$$-1.5<(R3+R2)/(R3-R2)<-0.6 \qquad (2').$$

3. The endoscopic objective lens as claimed in claim 1, wherein the endoscopic objective lens satisfies a conditional expression (1") given below:

$$27<vd2-vd1<58 \qquad (1').$$

4. The endoscopic objective lens as claimed in claim 1, wherein the endoscopic objective lens satisfies a conditional expression (2") given below:

$$-1.4<(R3+R2)/(R3-R2)<-0.7 \qquad (2'').$$

5. The endoscopic objective lens as claimed in claim 1, wherein the endoscopic objective lens satisfies a conditional expression (5) given below:

$$|D1/R2|1<0.10 \qquad (5)$$

where
D1: center thickness of the first lens.

6. The endoscopic objective lens as claimed in claim 1, wherein the endoscopic objective lens satisfies a conditional expression (6) given below:

$$0.80 < Bf/f < 1.38 \tag{6}$$

where

Bf: back focus of the entire system, and f: focal length of the entire system.

7. The endoscopic objective lens as claimed in claim 1, wherein the endoscopic objective lens satisfies a conditional expression (7) given below:

$$20 < vdp - vdn < 40 \tag{7}$$

where vdp: Abbe number of the positive lens of the cemented lens in the second lens group with respect to the d-line, and vdn: Abbe number of the negative lens of the cemented lens in the second lens group with respect to the d-line.

8. The endoscopic objective lens as claimed in claim 1, wherein the endoscopic objective lens satisfies conditional expressions (8) and (9) given below:

$$1.85 < Nd1 < 1.92 \tag{8}$$

$$35 < vd1 < 45 \tag{9}$$

where

Nd1: refractive index of the first lens with respect to the d-line, and vd1: Abbe number of the first lens with respect to the d-line.

9. An endoscope equipped with the endoscopic objective lens as claimed in claim 1.

10. An endoscopic objective lens, consisting essentially of a first lens group having a negative refractive power, a stop, and a second lens group having a positive refractive power, disposed in order from the object side, wherein:

the first lens group is composed of a cemented lens formed of a first lens and a second lens with a concave surface on the image side cemented in order from the object side;

the second lens group is composed of a positive single third lens and a cemented lens formed of a fourth lens and a fifth lens, either of which being a positive lens and the other being a negative lens, and having a positive refractive power as a whole, disposed in order from the object side; and the endoscopic objective lens satisfies conditional expressions (3") and (4) given below:

$$6 < |R2/R3| < 20 \tag{3"}$$

$$0.40 < |DS \times fG1/(f \times (DS - fG1))| < 0.60 \tag{4}$$

where

R2: radius of curvature of the object side surface of the second lens,

R3: radius of curvature of the image side surface of the second lens,

DS: distance on the optical axis from the object side surface of the first lens to the stop, fG1: focal length of the first lens group, and f: focal length of the entire system.

11. The endoscopic objective lens as claimed in claim 10, wherein the endoscopic objective lens satisfies a conditional expression (4') given below:

$$0.45 < |DS \times fG1/(f \times (DS - fG1))| < 0.55 \tag{4'}$$

12. The endoscopic objective lens as claimed in claim 10, wherein the endoscopic objective lens satisfies a conditional expression (4") given below:

$$0.48 < |DS \times fG1/(f \times (DS - fG1))| < 0.53 \tag{4"}$$

13. The endoscopic objective lens as claimed in claim 10, wherein the endoscopic objective lens satisfies a conditional expression (5) given below:

$$|D1/R2|1 < 0.10 \tag{5}$$

where

D1: center thickness of the first lens.

14. The endoscopic objective lens as claimed in claim 10, wherein the endoscopic objective lens satisfies a conditional expression (6) given below:

$$0.80 < Bf/f < 1.38 \tag{6}$$

where

Bf: back focus of the entire system, and f: focal length of the entire system.

15. The endoscopic objective lens as claimed in claim 10, wherein the endoscopic objective lens satisfies a conditional expression (7) given below:

$$20 < vdp - vdn < 40 \tag{7}$$

where vdp: Abbe number of the positive lens of the cemented lens in the second lens group with respect to the d-line, and vdn: Abbe number of the negative lens of the cemented lens in the second lens group with respect to the d-line.

16. The endoscopic objective lens as claimed in claim 10, wherein the endoscopic objective lens satisfies conditional expressions (8) and (9) given below:

$$1.85 < Nd1 < 1.92 \tag{8}$$

$$35 < vd1 < 45 \tag{9}$$

where

Nd1: refractive index of the first lens with respect to the d-line, and vd1: Abbe number of the first lens with respect to the d-line.

17. An endoscope equipped with the endoscopic objective lens as claimed in claim 10.

* * * * *